United States Patent [19]

Kole et al.

[11] Patent Number: 5,114,409
[45] Date of Patent: May 19, 1992

[54] BLANK FOR AND METHOD OF FABRICATING A NEEDLE CAP FINGER GUARD

[75] Inventors: Richard L. Kole, New Hempstead; Bernard Cohen, Spring Valley, both of N.Y.

[73] Assignee: Design Opportunity Corp., New City, N.Y.

[21] Appl. No.: 644,827

[22] Filed: Jan. 23, 1991

[51] Int. Cl.$^5$ .............................................. A61M 5/32
[52] U.S. Cl. ....................................... 604/192; 604/198; 428/36.91; 428/134
[58] Field of Search ............... 604/110, 192, 198, 263; 425/36.91, 76, 134, 192

[56] References Cited

U.S. PATENT DOCUMENTS

| | | | |
|---|---|---|---|
| 3,825,463 | 7/1974 | Amann | 428/134 |
| 4,139,009 | 2/1979 | Alvarez | 604/198 |
| 4,223,058 | 9/1980 | Citron | 428/192 X |
| 4,320,868 | 3/1982 | Petersson | 229/75 |
| 4,333,221 | 6/1982 | Hayashi | 29/413 |
| 4,573,975 | 3/1986 | Frist et al. | 604/192 |
| 4,627,994 | 12/1986 | Welsch | 428/41 |
| 4,654,034 | 3/1987 | Masters et al. | 604/192 |
| 4,735,618 | 4/1988 | Hagen | 604/192 |
| 4,767,412 | 8/1988 | Hymanson | 604/192 |
| 4,782,841 | 11/1988 | Lopez | 128/764 |
| 4,859,515 | 8/1989 | Pothetes | 428/40 |
| 4,911,694 | 3/1990 | Dolan | 604/198 |
| 4,935,013 | 6/1990 | Haber et al. | 604/192 |
| 4,998,922 | 3/1991 | Kuracina et al. | 604/192 |
| 5,069,669 | 12/1991 | Kole | 604/198 |

Primary Examiner—John D. Yasko
Assistant Examiner—Adam J. Cermak
Attorney, Agent, or Firm—Brooks Haidt Haffner & Delahunty

[57] ABSTRACT

A rhomboid piece of paper and plastic laminate has a central rhomboid region scored with parallel lines of weakening. Border regions are provided with appropriate layers of adhesive such that when the blank is wrapped around a needle cap, the border region nearest the open end of the cap bonds to the cap and provides a first circumferentially continuous end band, while the border region nearest the closed end of the cap provides a second end band which is axially moveable relative to the cap. The two end bands are joined by a plurality of longitudinally extending circumferentaily contiguous regions which separate into strips which project radially to form an umbrella-like structure when the second end band is urged toward the first end band. The strips extend along a slight helix angle before formation of the umbrella-like structure. For increased protection a second blank having a reversed rhomboid shape but being otherwise generally similar to the first blank can either be wrapped around the tube produced by the first blank, or joined to the first blank and wrapped simultaneously.

22 Claims, 5 Drawing Sheets

BLANK FOR AND METHOD OF FABRICATING A NEEDLE CAP FINGER GUARD

BACKGROUND OF THE INVENTION

The present invention relates to a finger guard for the needle cap that encloses a hypodermic or similar needle for preventing inadvertent and accidental needle sticks.

In the copending U.S. patent application of Richard L. Kole, Ser. No. 07/448,674, filed Dec. 11, 1989, now U.S. Pat. No. 5.069,669, there is disclosed a sleeve with a plurality of contiguous longitudinally oriented strips between end bands that is secured at one end to a cap for a hypodermic needle. The sleeve is constructed to bulge radially outwardly when its ends are slid longitudinally toward each other thereby forming a finger guard to protect against needle sticks. The sleeve is described as consisting of a tubular element, but no particular method is described for producing the sleeve.

SUMMARY OF THE PRESENT INVENTION

It is, therefore, an object of the present invention to provide an efficient and economical form of construction for a needle guard of the type described and claimed in the above-mentioned application.

It is another object of the present invention to provide a blank from which the needle guard can be constructed.

Yet another object of the present invention is to provide an improved needle guard configuration.

In accordance with one aspect of the present invention there is provided a blank for providing a needle cap with a finger guard upon wrapping the blank about the needle cap, the blank comprising at least one rhomboid piece of flexible sheet material that is resistant to piercing by a needle and is bounded by first and second pairs of parallel side edges. The piece of material is divided into a central rhomboid region and first and second border regions where the border regions border, respectively, each of one pair of the parallel side edges of said central region, each border region being also coextensive with and adjacent a corresponding one of the first pair of parallel side edges of the piece of material. Substantially the entire area of the central rhomboid region is scored with substantially equidistantly spaced parallel lines of weakening extending from the first border region to the said second border region. The first border region is provided on one side of the blank with a stripe of an adhesive substantially coextensive with the first border region at least over the length thereof. The second border region has along an end portion on one side of the blank an area overlaid with an adhesive layer. The adhesive stripe and layer are disposed such that the stripe joins the blank to a needle cap as the blank is wrapped around the cap, and the layer of adhesive secures the second border region to an underlying border portion when wrapping of the blank is completed. When wrapping of the blank is completed a tubular element is formed having first and second circumferentially continuous end sections joined by a plurality of longitudinally extending circumferentially contiguous regions which separate into strips which project radially to form an umbrella-like structure when the end sections are urged axially toward one another.

In accordance with another aspect of the present invention there is provided a finger guard mounted on a needle cap in which at least one blank as mentioned above is wrapped around the needle cap which has an open end and a closed end. The blank is oriented with the first pair of side edges of the piece of material lying in planes normal to the longitudinal axis of the needle cap, the circumferentially continuous end section formed by the first border region is disposed about and joined to the end cap adjacent the open end, and the circumferentially continuous end section formed by the second border region is disposed about the end cap adjacent the closed end axially slidingly thereupon.

BRIEF DESCRIPTION OF THE DRAWINGS

The invention will be understood better after reading the following detailed description of the presently preferred embodiments with reference to the appended drawings in which.

Throughout the various figures of the drawings the same reference numerals are used to designate the same or similar parts.

DETAILED DESCRIPTION OF THE PRESENTLY PREFERRED EMBODIMENTS

Figure 5:
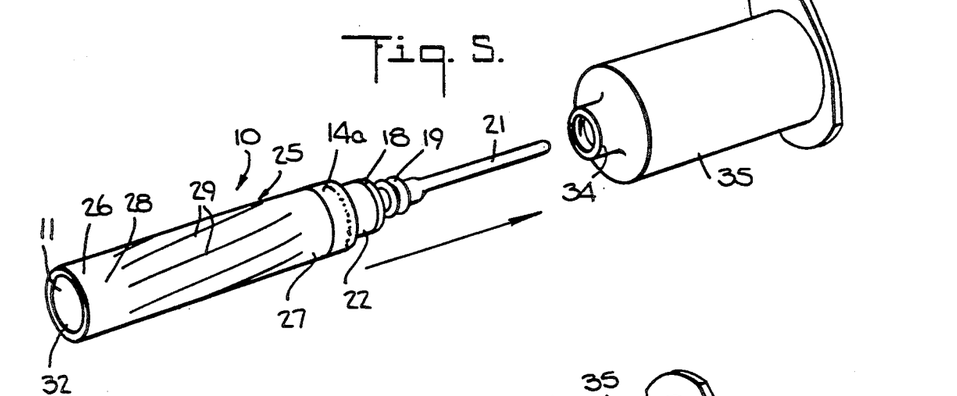
FIG. 5 is a perspective view showing the uncapped assembly of FIGS. 3 and 4 being inserted into a tube-receiving cylinder.
Figure 6:
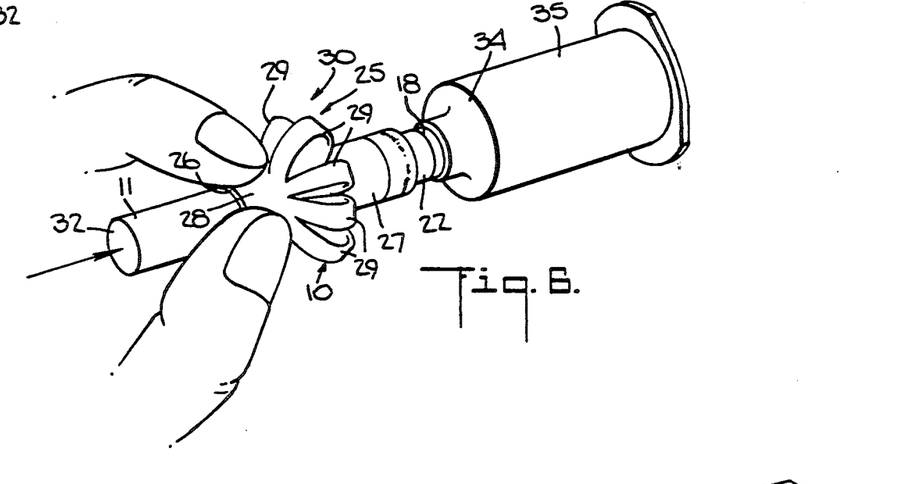
FIG. 6 is a perspective view showing the formation of a radially expanded guard during assembly of the needle and cylinder, here as a result of axial movement.
Figure 7:
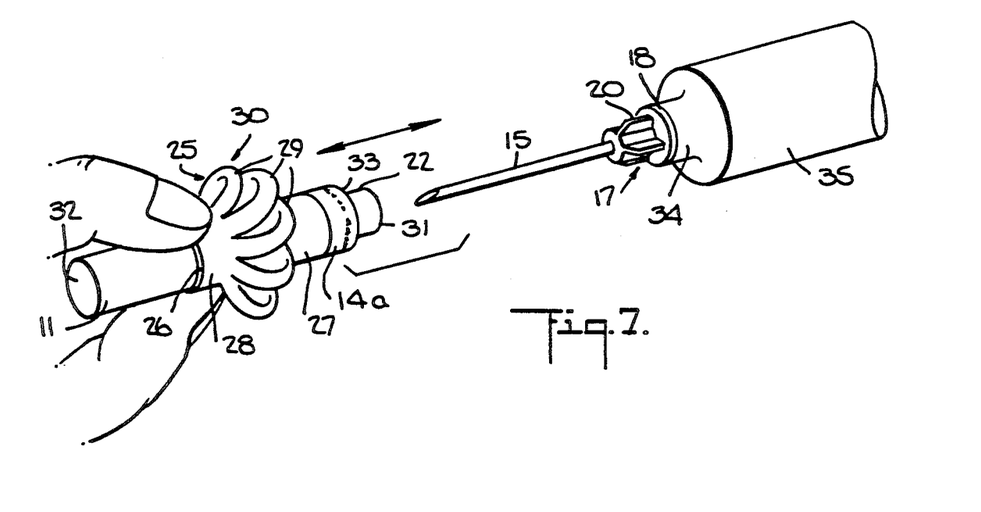
FIG. 7 is an exploded perspective view showing both the removal and the replacement of the needle cap for the needle that is inserted into the body of a patient.

Referring to the drawings, and particularly to FIGS. 1 to 7 which have been copied from the aforesaid pending application by way of background, there is shown, designated generally by the reference numeral 10, a double pointed multiple sample hypodermic needle packaged within a sealed enclosure consisting of first and second caps 11 and 12 with their junction 13 covered by a paper sealing band 14. First and second hollow needles, 15 and 16, project in opposite directions along a common longitudinal axis from an intermediate body structure 17. The body structure 17 has a generally centrally located radial flange 18, an externally threaded extension 19 on one side of the flange 18, and a cap-engaging extension 20 on the other side of the flange 18. The first cap, 11, encloses the hollow needle 15 and engages the cap engaging extension 20, which is fluted as seen in FIG. 7, while the second cap, 12, encloses the hollow needle 16 and the externally threaded extension 19 and telescopes over the radial flange 18 and over an area 22 at the open end of cap 11 that has a reduced outside diameter equal to that of the flange 18. The inside diameter of the mouth 23 of the cap 12 is dimensioned to make a snug but sliding fit over flange 18 and area 22. The reduced diameter area 22 terminates at a shoulder 33 on cap 11 (see FIGS. 3 and 4) which is engaged by the end of cap 12 and defines the juncture 13. Covering needle 16 is an elastomeric pierceable self-sealing sheath 21. The needle assembly described so far represents well known prior art.

As described in the aforementioned pending application, there is provided a finger guard 25 consisting of a tubular element or sleeve 26 of flexible needle-puncture-resistant material having first and second circumferentially continuous end sections, 27 and 28, joined by a plurality of longitudinally extending circumferentially contiguous strips 29 which strips, when the end sections 27 and 28 are urged axially toward one another, project radially, as best seen in FIGS. 6 and 7, to form an umbrella-like structure 30. The tubular element 26 is disposed concentrically about the tubular cap 11, which cap has an open end 31 (see FIG. 7) and a closed end 32. The end section 27 of the sleeve 26 is secured to the cap 11 in the vicinity of the open end 31, that is, adjacent the shoulder 33 bordering the reduced diameter area 22.

Figure 3:
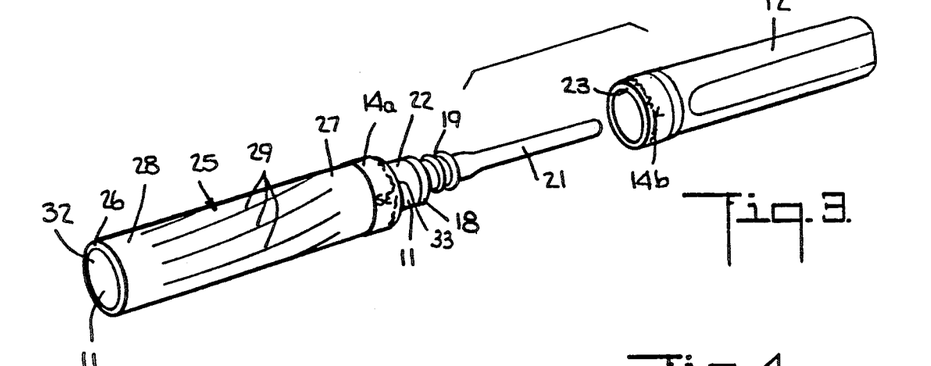
FIG. 3 is an exploded perspective view showing removal of one of the caps exposing a needle sheathed in a pierceable self-sealing elastomeric sheath.
Figure 4:
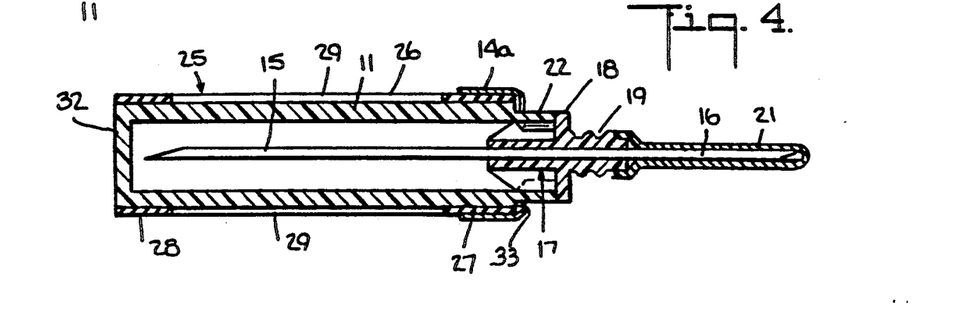
FIG. 4 is a longitudinal sectional view, similar to FIG. 2, but with the cap removed as shown in FIG. 3.

When using the hypodermic needle 10 the sleeve element 26 is gripped with the fingers of one hand while the cap 12 is gripped by the fingers of the other hand. Through a combination of relative counterrotation and axial separation, the seal 14 is broken and the cap 12 removed exposing the sheathed needle 16 as shown in FIG. 3. Next, gripping the sleeve element 26 near or at the end section 28, the needle 16 is inserted, as shown in FIG. 5, into the internally threaded boss 34 at the base of cylinder 35. The threaded extension 19 is engaged with the threads in boss 34 and threadedly assembled. While rotating the needle 10 to engage the mating threads, the section 28 of sleeve element 26 can be urged along cap 11 toward the stationary or fixed section causing the strips 29 to buckle and project radially outwardly.

Figure 1:
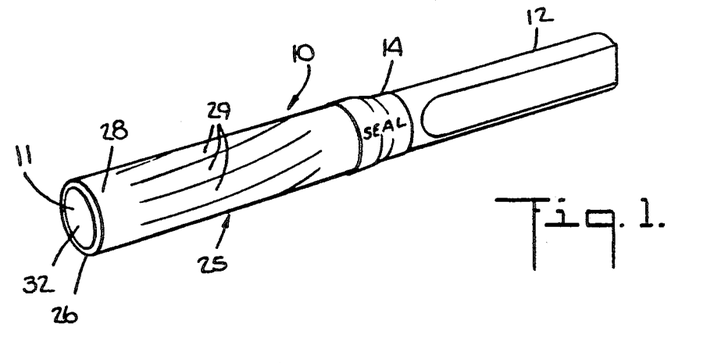
FIG. 1 is a perspective view of a double pointed hypodermic needle assembly with caps enveloping the needles and joined by a sealing band.
Figure 2:
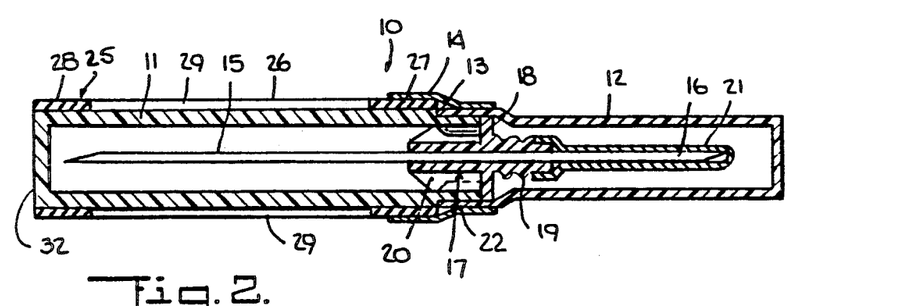
FIG. 2 is a longitudinal sectional view of the assembly of FIG. 1.

As seen in FIGS. 1, 3 and 5, the strips 29 are formed along helical lines. Because of this helical disposition, the "petals" 29 formed during the step illustrated in FIG. 6, produce a slightly fanned array as shown in FIG. 7. However, as described in said application, the guard has appreciable gaps in the spaces between the strip-petals 29. To eliminate these gaps, the end section 28 of sleeve element 26 was rotated in the clockwise direction, the same direction used to engage the threads, until the petals assume the condition shown in FIG. 7. At this point the cap 11 can be removed, as seen in FIG. 7, to expose needle 15 which can then be inserted into the patient.

When sampling is complete the needle 15 is withdrawn from the patient and the cap 11, with guard 25 expanded, is returned over needle 15 to engage extension 20. As illustrated, the expanded structure 30 formed by guard 25 protects the fingers of the operator from being accidentally stuck by the now contaminated needle 15.

The previously described procedure is now reversed and the needle assembly 10 is separated from cylinder 35 as shown in FIG. 5. At this stage the sheath 21 has re-covered the needle 16. The cap 12 can be replaced and the assembly disposed of in the normal manner after the sleeve 26 has been restored to its initial condition as shown in FIG. 1.

Figure 8:
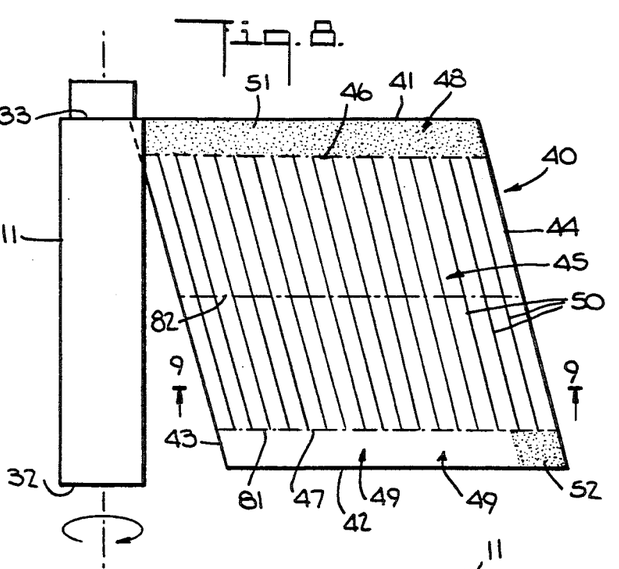
FIG. 8 is a diagrammatic view showing details of a blank constructed in accordance with the present invention and indicating the relationship relative to a needle cap as the blank is about to be wrapped therearound, the arrows showing the direction of movement.
Figures 9, 10, 11, 12, 13:
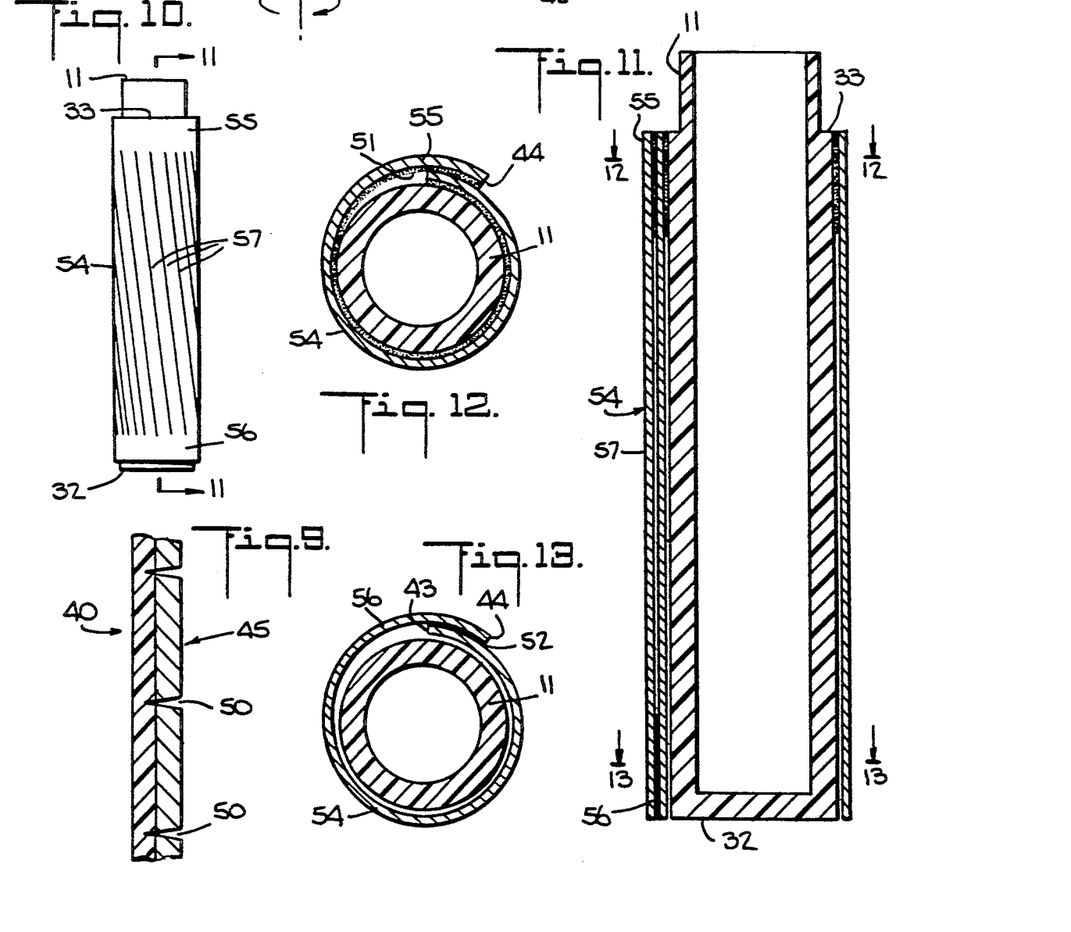
FIG. 9 is a fragmentary sectional view to an enlarged scale taken along the line 9—9 in FIG. 8.
FIG. 10 is a plan view showing the blank of FIG. 8 fully wrapped about the needle cap thereby forming a tubular structure concentric with the cap.
FIG. 11 is an enlarged longitudinal sectional view taken along the line 11—11 in FIG. 10.
FIG. 12 is a transverse sectional view taken along line 12—12 in FIG. 11 and showing the bonding of the guard to the cap near the cap open end.
FIG. 13 is a transverse sectional view taken along line 13—13 in FIG. 11.

Having reviewed the configuration of the finger guard and its operation as disclosed in the prior application, attention can now be directed to FIG. 8 wherein a blank is illustrated that embodies the present invention.

The blank is designated generally by the reference numeral 40. Blank 40 is formed from flexible sheet material that is resistant to piercing by a needle. At present it is preferred to use a plastic and paper laminate where the plastic is either mylar or an acetate. The overall thickness of the material is preferably in the range of about 0.004" to 0.005" with each of the plastic and paper layers ranging from about 0.002" to 0.003" in thickness.

As shown, the blank 40 is rhomboid shape bounded by a first pair of parallel side edges, 41, 42, and a second pair of parallel side edges, 43, 44. The piece 40 is divided into a central rhomboid region 45 and first and second border regions, 48 and 49 where the border regions 48 and 49 border, respectively, each of one pair of the parallel side boundaries or margins, 46, 47, of the central region, 45. Each of the border regions 48 and 49 is also coextensive with and adjacent a corresponding one of the edges 41 and 42 of the piece of material 40. Substantially the entire area of the central rhomboid region 45 is scored with substantially equidistantly spaced parallel lines of weakening, 50, extending from first border region, 48, to second border region, 49. The first border region, 48, is provided on one side of the blank 40 with a stripe 51 of a pressure sensitive adhesive substantially coextensive with the border region 48 at least over the length thereof. As will appear from a complete reading of the specification it is not necessary that the width of the adhesive stripe be coextensive with the width of the border region. The second border region, 49, has along an end portion on one side of the blank 40 an area overlaid with a pressure sensitive adhesive layer 52. The adhesive stripe 51 and layer 52 are disposed such that the stripe 51 joins the blank 40 to the needle cap 11 as the blank 40 is wrapped around the cap 11. The layer 52 of adhesive secures the second border region, 49, to an underlying border portion when wrapping of the blank 40 is completed. As seen in FIGS. 10 to 13, wrapping of the blank 40 about the cap 11 in the direction of the arrow in FIG. 8 produces a tubular element 54 having first and second circumferentially continuous end sections, 55 and 56, joined by a plurality of longitudinally extending circumferentially contiguous regions 57 which separate into strips which project radially as shown in FIGS. 6 and 7 to form the umbrella-like structure 30 when the end section 56 is urged axially toward the end section 55. It should be understood that the portion of region 49 of blank 40 that is free of adhesive is long enough to completely encircle cap 11 such that none of the adhesive layer 52 contacts the cap 11.

In general, the adhesive stripe 51 and layer 52 will be applied to the paper side of the plastic and paper laminate constituting blank 40. This will place the plastic layer outermost when the blank is wrapped around a needle cap.

In order to induce the tubular element 54 to fold and expand as shown in FIGS. 6 and 7, the blank 40 can be provided, additionally, with embossed fold inducing lines 80, 81 and 82. As shown in FIG. 8, the lines 80 and 81 border the respective regions 48 and 49, while the line 82 is located midway between lines 80 and 81.

For a conventional needle cap having a diameter on the order of 0.4" the blank 40 may actually be rhombic and have equal length sides of about 1⅜". This assumes that the length of the needle cap from the closed end 32 to the shoulder 33 is about 1⅜" and that approximately ¼" overlap is desired as between edges 43 and 44 when the blank 40 is completely wrapped.

Figure 14:
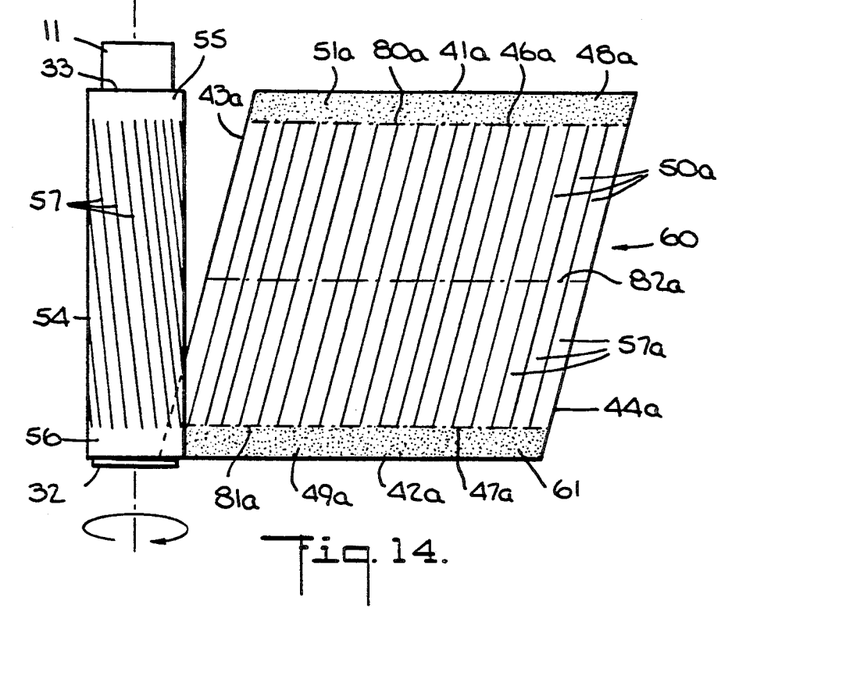
FIG. 14 is a view similar to FIG. 8 showing another configuration of the blank used to develop a second guard layer over the layer of FIG. 10.

While the embodiment of FIG. 8 produces an effective guard, the guard can be improved by applying a second blank around the first tubular element 54 as shown diagrammatically in FIG. 14. Preferably, the blank 60 is as shown in FIG. 14 with the rhomboid reversed from that shown in FIG. 8. In order to avoid repeating the description of the blank which is in most respects similar to blank 40, similar or corresponding parts in FIG. 14 are merely designated by the same reference numeral followed by the letter "a". Side edges 41a and 42a are to be oriented normal to the longitudinal axis of the cap 11. Edges 43a and 44a are inclined in the opposite direction from edges 43 and 44, and weakening lines 50a are parallel to edges 43a and 44a. In addition, an adhesive stripe 61 is applied along region 49a coextensive therewith rather than localized as was layer 52. This is desireable so as to join region 49a of blank 60 to and about the end section 56 of tube 54 when blank 60 is wrapped thereover. Operation of the guard of FIG. 14 is essentially the same as that of FIG. 8 with the strips 57a separating and buckling radially outwardly when the resulting tubular element has its free end urged toward the end secured to cap 11. Embossed lines 80a, 81a and 82a can be included to encourage the desired radial expansion.

For both blanks 40 and 60, the preferred acute rhomboid angle is between about 70° and 85° with about 75° presently preferred. The preferred spacing between the weakening lines 50 or 50a is between about ⅛" and ⅜". The presently preferred spacing is about ¼".

Figure 15:
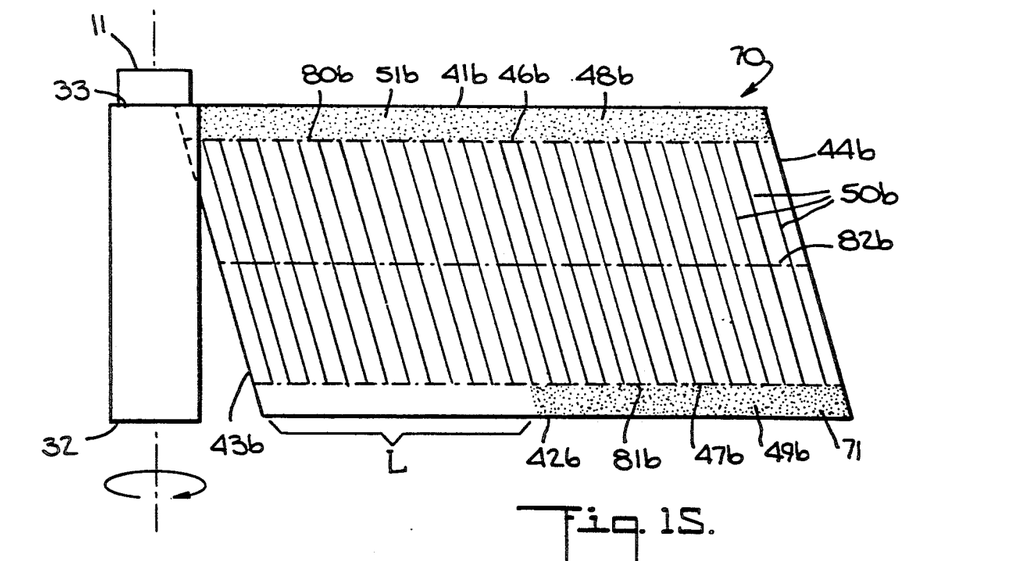
FIG. 15 is a plan view of a modified blank intended to enwrap a needle cap with approximately two turns or more.

Another embodiment is shown in FIG. 15 wherein the rhomboid blank 70 is increased in the wrapping direction such that it will encircle the cap 11 at least close to two times if not more. Similar parts are here designated with an appended letter "b".

In blank 70 the region 49b is free from adhesive for at least a distance $L = \pi D$ where D is the diameter of the cap 11. This provides a portion long enough to fully encircle the cap 11 without adhering thereto. However, the remainder of region 49b is coated with an adhesive layer 71 to bond to the underlying portion of region 49b as the blank is further wrapped about cap 11. For best results the spacing of the lines 50b should be selected so that the strips formed therebetween do not fall into exact registration with underlying strips as the blank 70 makes more than one wrap around the cap 11.

Figure 16:
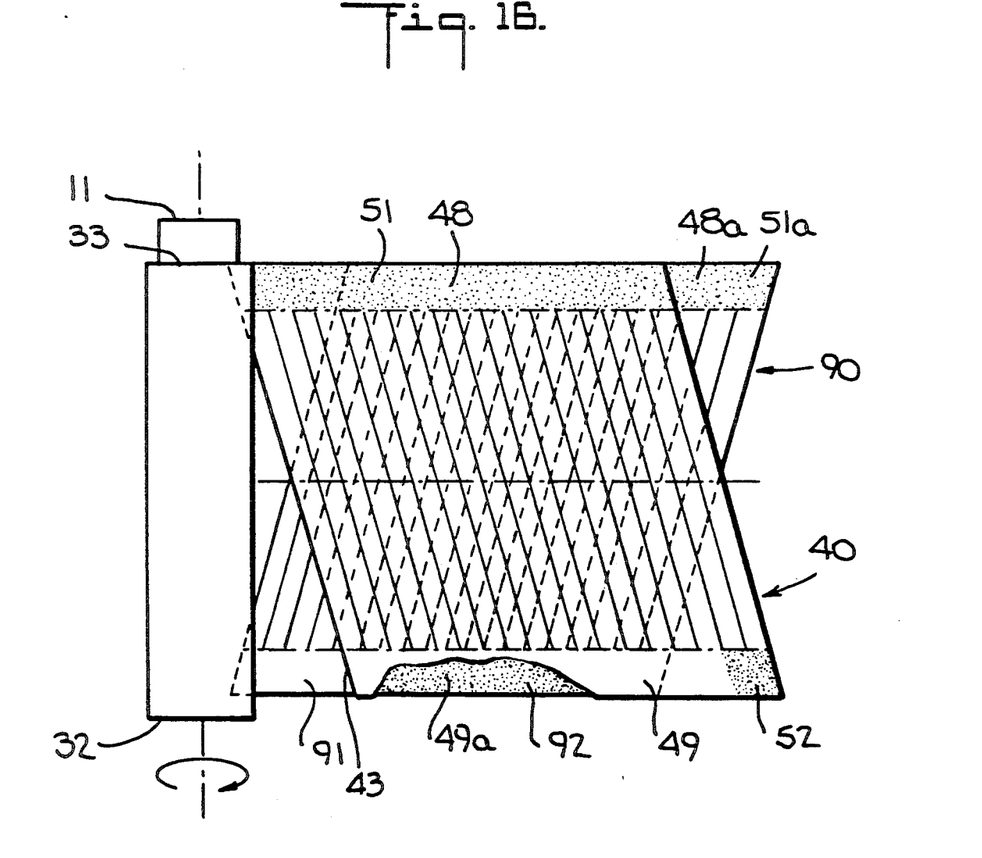
FIG. 16 is a view similar to FIG. 8 showing a further modification in which blanks similar to those shown in FIGS. 8 and 14 are joined together in the overlapping edge regions so as to provide an alternative method of constructing a double layered guard similar to that shown in FIG. 14.

Referring now to FIG. 16, there is shown diagrammatically a further modification of the blank for producing a double layered sleeve similar to that described with reference to FIG. 14. Instead of sequentially wrapping two blanks of opposite rhomboid angle, two such blanks are joined together as shown in FIG. 16 and wrapped simultaneously around the needle cap 11. The rhomboid piece of sheet material 40 is essentially identical to the blank 40 in FIG. 8, having the same border regions 48 and 49 provided with the same adhesive stripe 51 and layer 52.

The rhomboid piece of sheet material 90 is very similar to the piece of sheet material 60 shown in FIG. 14. The border region 48a with adhesive stripe 51a is the same as well as the central rhomboid region. Sheet 90, however, differs from sheet 60 in that the area 91 in border region 49a which extends beyond the edge 43 of sheet 40 is free of the adhesive 92. The adhesive 92 is confined to the area of overlap between border regions 49 and 49a. Thus, sheets 40 and 90 are joined together to provide a composite blank which when wrapped around the cap 11 produces a double layer sleeve essentially the same as that produced with the procedure described with reference to FIG. 14.

In all of the embodiments the production of the weakening lines 50, 50a and 50b can be accomplished in any known manner. At present it is preferred to cut through the plastic layer of the laminate while leaving the paper layer essentially intact. However, it may be desirable to sever the paper layer while leaving the plastic layer intact or the lines can be produced by spaced perforations or the like, all of which is contemplated within the term "scoring".

While only a double needle assembly has been illustrated in the drawings, it should be apparent that the invention can be applied to needle caps intended for use with single or double needle assemblies and to one or both caps in a double needle structure.

Having described the present invention with reference to the presently preferred embodiments thereof, it is to be understood that various changes in construction are contemplated as will occur to those skilled in the subject art without departing from the true spirit of the invention as defined in the appended claims.

What is claimed is:

1. A blank for providing a needle cap, having a longitudinal axis and both an open end and a closed end with a finger guard upon wrapping the blank about the needle cap, said blank comprising at least one rhomboid piece of flexible sheet material that is resistant to piercing by a needle and is bounded by first and second pairs of parallel side edges, said piece of material being divided into a central rhomboid region and first and second border regions where the border regions border, respectively, each of one pair of the parallel side boundaries of said central region, each border region being also coextensive with and adjacent a corresponding one of said first pair of parallel side edges of the piece of material, substantially the entire area of said central rhomboid region being scored with substantially equidistantly spaced parallel lines of weakening extending from said first border region to said second border region, said first border region being provided on one side of said blank with a stripe of an adhesive substantially coextensive at least over the length thereof with said first border region, said second border region having along an end portion on one side of said blank an area overlaid with an adhesive layer, said adhesive stripe and layer being disposed such that said stripe joins said blank to a needle cap as said blank is wrapped around said cap, and said layer of adhesive secures said end portion of the second border region to an underlying border portion when wrapping of said blank is completed, whereby when wrapping of said blank is completed a tubular element is formed having first and second circumferentially continuous end sections joined by a plurality of longitudinally extending circumferentially contiguous regions which separate into strips which project radially to form an umbrella-like structure when said end sections are urged axially toward one another.

2. A blank according to claim 1, wherein the acute angles of said rhomboid piece of flexible sheet material are within the range of 70° to 85°.

3. A blank according to claim 2, wherein said parallel lines of weakening are parallel to said second pair of side edges of the piece of material.

4. A blank according to claim 1, wherein said parallel lines of weakening are parallel to said second pair of side edges of the piece of material.

5. A blank according to claim 4, wherein there are two of said rhomboid pieces of material, oppositely oriented relative to each other, joined together within said border regions with said border regions overlapping substantially equally along each of said first pair of parallel side edges of the respective pieces of material, whereby in the tubular element formed upon said wrapping of the blank the respective lines of weakening follow oppositely directed helical paths.

6. A blank according to claim 1, wherein said parallel lines of weakening are spaced apart normal to said lines of weakening a distance within the range of about ¼ to ⅜ inches.

7. A blank according to claim 6, wherein said parallel lines of weakening are parallel to said second pair of side edges of the piece of material.

8. A blank according to claim 7, wherein the acute angles of said rhomboid piece of flexible sheet material are within the range of 70° to 85°.

9. A blank according to claim 6, wherein the acute angles of said rhomboid piece of flexible sheet material are within the range of 70° to 85°.

10. The combination of at least one blank according to claim 1 wrapped around said needle cap, said blank being oriented with said first pair of side edges of the piece of material lying in planes normal to the longitudinal axis of said needle cap, the circumferentially continuous end section formed by said first border region being disposed about and joined to said needle cap adjacent said open end, and the circumferentially continuous end section formed by said second border region being disposed about said needle cap adjacent said closed end axially slidingly thereupon.

11. The combination according to claim 10, wherein two of said blanks are wrapped succesively about said needle cap.

12. The combination according to claim 11, wherein said two blanks are oppositely oriented such that when wrapped about the needle cap the respective lines of weakening follow oppositely directed helical paths.

13. A finger guard according to claim 12, wherein said parallel lines of weakening in said blank are parallel to said second pair of side edges of the piece of material.

14. A finger guard according to claim 13, wherein said parallel lines of weakening are spaced apart normal to said lines of weakening a distance within the range of about ¼ to ⅜ inches.

15. A finger guard according to claim 14, wherein the acute angles of said rhomboid piece of flexible sheet material are within the range of 70° to 85°.

16. A finger guard according to claim 10, wherein said parallel lines of weakening in said blank are parallel to said second pair of side edges of the piece of material.

17. A finger guard according to claim 16, wherein said parallel lines of weakening are spaced apart normal to said lines of weakening a distance within the range of about ¼ to ⅜ inches.

18. A finger guard according to claim 17, wherein the acute angles of said rhomboid piece of flexible sheet material are within the range of 70° to 85°.

19. A finger guard according to claim 10, wherein two of said rhomboid pieces of material, oppositely oriented relative to each other, are joined together within said border regions which overlap substantially equally along each of said first pair of parallel side edges of the respective pieces of material such that when wrapped about the needle cap the respective lines of weakening follow oppositely directed helical paths.

20. A finger guard according to claim 19, wherein said parallel lines of weakening in each said piece of material are parallel to said respective second pair of side edges of the corresponding piece of material.

21. A finger guard according to claim 20, wherein said parallel lines of weakening are spaced apart normal to said lines of weakening a distance within the range of about ¼ to ⅜ inches.

22. The combination according to claim 21, wherein the acute angles of each rhomboid piece of flexible sheet material are within the range of 70° to 85°.

* * * * *

UNITED STATES PATENT AND TRADEMARK OFFICE
CERTIFICATE OF CORRECTION

PATENT NO. : 5,114,409

DATED : May 19, 1992

INVENTOR(S) : Richard L. Kole et al.

It is certified that error appears in the above-identified patent and that said Letters Patent is hereby corrected as shown below:

Column 6, line 52, a comma (,) should be inserted before "with".
Column 8, lines 14, 17, 21, 24, 27, 31, 34, 42, 46, each occurrence, "A finger guard" should read --The combination--.

Signed and Sealed this

Twenty-fourth Day of August, 1993

*Attest:*

BRUCE LEHMAN

*Attesting Officer*   Commissioner of Patents and Trademarks